(12) United States Patent
Yoda et al.

(10) Patent No.: US 8,158,115 B2
(45) Date of Patent: *Apr. 17, 2012

(54) COPOLYMER AND DETERGENT COMPOSITION EMPLOYING IT

(75) Inventors: Shoya Yoda, Yokkaichi (JP); Yuko Yoda, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/172,295

(22) Filed: Jun. 29, 2011

(65) Prior Publication Data

US 2011/0256086 A1  Oct. 20, 2011

Related U.S. Application Data

(63) Continuation of application No. 11/997,838, filed as application No. PCT/JP2006/315332 on Aug. 2, 2006, now Pat. No. 8,003,088.

(30) Foreign Application Priority Data

| Aug. 4, 2005 | (JP) | 2005-227247 |
|---|---|---|
| Aug. 4, 2005 | (JP) | 2005-227248 |
| Aug. 4, 2005 | (JP) | 2005-227249 |
| Aug. 4, 2005 | (JP) | 2005-227250 |

(51) Int. Cl.
*A61K 8/37* (2006.01)
*A61K 8/42* (2006.01)
*C11D 1/02* (2006.01)
*C11D 1/62* (2006.01)
*C11D 3/37* (2006.01)
*C08F 26/02* (2006.01)
*C08F 220/34* (2006.01)
*C08F 220/58* (2006.01)

(52) U.S. Cl. ............ 424/70.17; 424/70.16; 424/70.22; 424/70.28; 510/122; 510/123; 510/127; 510/156; 510/426; 510/466; 510/475; 510/504

(58) Field of Classification Search ............ 510/122, 510/123, 127, 156, 426, 466, 475, 504; 424/70.16, 424/70.17, 70.22, 70.28
See application file for complete search history.

(56) References Cited

U.S. PATENT DOCUMENTS

| 4,163,092 A | 7/1979 | Steckler |
| 4,218,554 A | 8/1980 | Foley, Jr. |
| 4,981,936 A | 1/1991 | Good et al. |
| 8,003,088 B2 * | 8/2011 | Yoda et al. ............ 424/70.17 |
| 2003/0170197 A1 | 9/2003 | Terazaki et al. |
| 2007/0167593 A1 | 7/2007 | Yoda et al. |

FOREIGN PATENT DOCUMENTS

| DE | 100 61 656 A1 | 6/2002 |
| GB | 1015795 | 1/1966 |
| JP | 59 024708 | 2/1984 |
| JP | 2000-144185 | 5/2000 |
| JP | 2000 178121 | 6/2000 |
| JP | 2003 34704 | 2/2003 |
| JP | 2003 277794 | 10/2003 |
| JP | 2004 307419 | 11/2004 |
| JP | 2005-075823 | 3/2005 |
| JP | 2005 75861 | 3/2005 |
| JP | 2007 522092 | 8/2007 |
| WO | WO 00/39176 | 7/2000 |
| WO | WO 02/060967 A1 | 8/2002 |
| WO | 2004 009662 | 1/2004 |
| WO | WO 2004/009662 | 1/2004 |

OTHER PUBLICATIONS

Notice of Reasons for Refusal issued Feb. 14, 2012, in Japanese Patent Application No. 2006-211273, filed Aug. 2, 2006 (with English-language Translation).

* cited by examiner

*Primary Examiner* — Brian P Mruk

(74) *Attorney, Agent, or Firm* — Oblon, Spivak, McClelland, Maier & Neustadt, L.L.P.

(57) ABSTRACT

A detergent composition, which imparts smoothness in finger-combing in rinsing after washing and smoothness, silky texture and non-stiffness to hair after application and drying is provided. The detergent composition comprises a copolymer having no cross-linking units and comprising constituting units corresponding to a cationic vinyl monomer (A) and constituting units corresponding to a specific vinyl monomer (B) having a hydroxyl group or an amide group, wherein the proportion of the constituting units corresponding to the cationic vinyl monomer (A) is from 25 to 45 mol % based on the entire constituting units constituting the copolymer.

10 Claims, No Drawings

COPOLYMER AND DETERGENT COMPOSITION EMPLOYING IT

This application is a continuation application of prior U.S. application Ser. No. 11/997,838, filed on Feb. 4, 2008, issued on Aug. 23, 2011, as U.S. Pat. No. 8,003,088, the disclosure of which is incorporated herein by reference in its entirety. The parent application is the National Stage of PCT/JP06/315332, filed Aug. 2, 2006, the disclosure of which is incorporated herein by reference in its entirety. The parent application claims priority to Japanese Application Nos. 2005-227247, 2005-227248, 2005-227249 and 2005-227250, all filed Aug. 4, 2005, the disclosures of which are incorporated herein by reference in their entireties.

TECHNICAL FIELD

The present invention relates to a copolymer and a detergent composition employing it.

BACKGROUND ART

In a detergent such as a shampoo or a body soap, a so-called conditioning agent is incorporated to improve the smoothness in washing or in combing or passing fingers through the hair after the washing, or the smoothness, flexibility, silky texture or other textures of the hair after drying. For example, it is known to incorporate cationic hydroxyethyl cellulose, cationic guar gum, a dimethyl diallyl ammonium chloride/acrylamide copolymer as a conditioning agent to a shampoo.

The shampoo having cationic hydroxyethyl cellulose or the like incorporated is good in finger-combing in rinsing, but after drying, the hair is likely to present a coarse or stiff texture. To overcome such a drawback, it has been studied, for example, to incorporate an oil or to use a surfactant in combination. Particularly, it is known to incorporate silicone oil, whereby the texture after drying will substantially change (e.g. JP-A-2003-212733 (U.S. 2003-0170197)).

Further, the conditioning agent is required to be adsorbed to the hair and accordingly, an amino acid-modified cationic polymer has been proposed as a conditioning agent which has stickiness or greasiness reduced while maintaining a proper adsorption property and which maintains a conditioning effect without being washed off in rinsing (e.g. JP-A-2003-034704).

DISCLOSURE OF THE INVENTION

Problems to be Solved by the Invention

However, according to a study by the present inventors, there has been a case where a higher conditioning effect is required. Further, in a case where silicone oil is incorporated to a hair cosmetic, it is required to add a substantial amount of e.g. cationic hydroxyethyl cellulose in order to let a sufficient amount of silicone oil deposit on the hair, whereby a coarse or stiff texture has been given simultaneously. Further, in the case of hair damaged by bleaching or hair-dyeing (hereinafter sometimes referred to as "damaged hair"), the amount of adsorption of silicone oil sometimes tended to be small, whereby no adequate conditioning effect was obtainable.

It is an object of the present invention to solve the above problems and to provide a detergent composition which is excellent in the smoothness in finger-combing in rinsing after washing and in the smoothness and silky texture after drying.

Means to Solve the Problems

In view of the above problems, the present inventors have conducted an extensive study and as a result, have found that by incorporating to a detergent composition a copolymer comprising constituting units corresponding to a cationic vinyl monomer and constituting units corresponding to a vinyl monomer having a specific structure, in a specific ratio, the finger-combing in rinsing after washing and the smoothness and silky texture after drying will be excellent. The present invention has been accomplished on the basis of this discovery.

Namely, the present invention provides the following.

1. A copolymer comprising constituting units corresponding to a cationic vinyl monomer (A) and constituting units corresponding to a vinyl monomer (B) of the formula (1) or (2), wherein the proportion of the constituting units corresponding to the cationic vinyl monomer (A) is from 25 to 45 mol % based on the entire constituting units constituting the copolymer:

$$CH_2=C(R^1)-CO-NR^2R^3 \qquad (1)$$

wherein $R^1$ is a hydrogen atom or a methyl group, and each of $R^2$ and $R^3$ which are independent of each other, is a hydrogen atom or a $C_{1-3}$ alkyl group, provided that the sum of carbon numbers of $R^2$ and $R^3$ is from 1 to 4, $$CH_2=C(R^4)-CO(O)-(CH_2)_a-(CHOH)_b-OH \qquad (2)$$

wherein $R^4$ is a hydrogen atom or a methyl group, a is an integer of from 1 to 4, and b is 0 or 1.

2. The copolymer according to the above 1, wherein the proportion of the constituting units corresponding to the vinyl monomer (B) is from 20 to 75 mol % based on the entire constituting units constituting the copolymer.

3. The copolymer according to the above 1 or 2, wherein the cationic vinyl monomer (A) is at least one monomer to represented by the formula (3):

$$CH_2=C(R^5)-CO-(O)_c-(NH)_{1-c}-(CH_2)_d-N^+R^6R^7R^9 \cdot X^- \qquad (3)$$

wherein $R^5$ is a hydrogen atom or a methyl group, each of $R^6$ and $R^7$ which are independent of each other, is a $C_{1-24}$ alkyl group, an aryl group or an aralkyl group, $R^8$ is a hydrogen atom, a $C_{1-24}$ alkyl group, an aryl group, an aralkyl group or $-CH_2-CH(OH)-CH_2-N^+R^9R^{10}R^{11} \cdot Y-$, each of $R^9$ to $R^{11}$ which are independent of one another, is a $C_{1-24}$ alkyl group, an aryl group or an aralkyl group, each of $X^-$ and $Y^-$ which are independent of each other, is an anion, c is 0 or 1, and d is an integer of from 1 to 10.

4. The copolymer according to the above 3, wherein as the cationic vinyl monomer (A), a monomer (A1) of the formula (3) wherein c is 1, and a monomer (A2) of the formula (3) wherein c is 0, are contained.

5. The copolymer according to the above 4, wherein the proportion of constituting units corresponding to the monomer (A1) is from 1 to 44 mold, the proportion of constituting units corresponding to the monomer (A2) is from 1 to 44 mol %, and the total of the proportions of the two is from 25 to 45 mol %, based on the entire constituting units constituting the copolymer.

6. The copolymer according to any one of the above 1 to 5, which has a weight average molecular weight of from 10,000 to 2,000,000.

7. The copolymer according to any one of the above 1 to 6, which contains no cross-linking agent as a constituting component.

8. The copolymer according to any one of the above 1 to 7, which contains at least constituting units corresponding to the vinyl monomer (B) of the formula (1).

9. A detergent composition comprising the copolymer as defined in any one of the above 1 to 8 and at least one surfactant.

10. The detergent composition according to the above 9, which contains, as the copolymer, at least a copolymer (C1) and a copolymer (C2), wherein the proportion of constituting units corresponding to the cationic vinyl monomer (A) in the entire constituting units constituting the copolymer (C2) is larger than the proportion of constituting units corresponding to the cationic vinyl monomer (A) in the entire constituting units constituting the copolymer (C1).

11. The detergent composition according to the above 9, which contains, as the copolymer, at least a copolymer (C3) and a copolymer (C4), wherein the copolymer (C3) is a copolymer comprising constituting units corresponding to a vinyl monomer of the formula (1) or (2) and constituting units corresponding to a monomer (A1) of the formula (3) wherein c is 1, and the copolymer (C4) is a copolymer comprising constituting units corresponding to a vinyl monomer of the formula (1) or (2) and constituting units corresponding to a monomer (A2) of the formula (3) wherein c is 0.

12. The detergent composition according to any one of the above 9 to 11, which contains, as the surfactant, at least an anionic surfactant.

13. The detergent composition according to the above 12, which comprises from 5 to 40 wt % of an anionic surfactant, from 0 to 10 wt %, in total, of at least one surfactant selected from the group consisting of an amphoteric surfactant, a nonionic surfactant and a semi-polar surfactant, and from 0.01 to 5 wt % of the copolymer.

14. The detergent composition according to any one of the above 9 to 13, which further contains a silicone oil and/or a higher alcohol.

15. The detergent composition according to any one of the above 9 to 14, which is used for hair.

Effects of the Invention

When incorporated to a detergent composition, the copolymer of the present invention is capable of improving slippage of the surface of the object to be cleaned such as the skin or the hair during washing. Further, after drying, the surface of the object to be cleaned is thereby protected, whereby the smoothness in rinsing or foaming will be secured, or finger-combing after towel-dry or the silky texture, non-stiffness or flexibility after drying will be excellent. Further, particularly high effects can be obtained when it is used in combination with an anionic surfactant.

Further, the detergent composition having the copolymer of the present invention incorporated, is excellent particularly in e.g. conditioning effects when used for the hair.

BEST MODE FOR CARRYING OUT THE INVENTION

Now, the present invention will be described in detail. In this specification, " . . . to . . . " is meant to include the numerical values before and after "to" as the lower limit and upper limit values. Further, the concentration and the viscosity in the present invention are represented by those at 25° C. unless otherwise specified.

The copolymer of the present invention comprises constituting units corresponding to a cationic vinyl monomer (A) and constituting units corresponding to a vinyl monomer (B) having a specific structure. Here, the proportion of the constituting units corresponding to the cationic vinyl monomer (A) in the entire constituting units constituting the copolymer is from 25 to 45 mol %.

When incorporated to a detergent composition, this copolymer exhibits excellent conditioning effects, and thus, the detergent composition containing it, presents excellent effects to the skin or hair, particularly not only to non-treated hair but also to damaged hair, such as smoothness or smooth finger-combing in rinsing and a dry texture or flexibility after drying.

In the copolymer, the constituting units corresponding to a cationic vinyl monomer (A) are likely to form a complex (a composite) with a surfactant commonly used in a detergent composition, particularly with an anionic surfactant. It is considered that the complex thus formed is present in such a state as re-dispersed and will deposit on the hair to cover it uniformly, thereby to present the smoothness, dry texture and flexibility to the skin or the hair.

On the other hand, in the copolymer, the constituting units corresponding to a vinyl monomer (B) represented by the formula (1) or (2) have an amide bond or a hydroxyl group and due to hydrophilicity derived therefrom, have an effect to impart hydrophilicity to the copolymer. It is considered that the water-solubility of the copolymer can thereby be maintained even when the copolymer forms a complex with a surfactant. Further, ones having an amide bond are considered to have an effect such that due to the hydrogen bond action with the skin and hair surface, the above complex tends to be readily adsorbed on the skin or hair. Accordingly, the vinyl monomer (B) is more preferably the one represented by the formula (1).

The proportion of the constituting units corresponding to the cationic vinyl monomer (A) in the entire constituting units constituting the copolymer is at least 25 mol %, whereby the copolymer contains cationic groups in an adequate amount. Accordingly, the copolymer tends to readily form a complex with a surfactant component, and the amount of adsorption on the hair increases, and for example, the smoothness or smooth finger-combing in rinsing, and the dry texture and flexibility after drying will be improved. The proportion is more preferably at least 26 mol %, more preferably at least 27 mol %.

However, the proportion of the constituting units corresponding to the cationic vinyl monomer (A) in the entire constituting units constituting the copolymer is at most 45 mol %, whereby the complex with the surfactant tends to be readily re-dispersible. Accordingly, the adhesion force to the hair, etc. can be sufficiently maintained, and for example, the smoothness and dry texture after drying can be maintained more effectively. The proportion is more preferably at most 42 mol %, further preferably at most 38 mol %, particularly preferably at most 35 mol %.

The proportion of the constituting units corresponding to the vinyl monomer (B) in the entire constituting units constituting the copolymer is preferably at least 20 mol %, whereby the adsorption force to the hair, etc. can be maintained more sufficiently, and the smoothness and silky texture after drying can be maintained more effectively. The proportion is more preferably at least 30 mol %, further preferably at least 40 mol %, most preferably at least 55 mol %.

However, the proportion of the constituting units corresponding to the vinyl monomer (B) in the entire constituting units constituting the copolymer is preferably at most 75 mol %, whereby the density of is cationic groups in the copolymer will be correspondingly high, and a more sufficient complex with an anionic surfactant may be formed. Accordingly, for example, the smoothness in rinsing of the washed hair can be maintained more effectively. The proportion is more preferably at most 70%.

The copolymer of the present invention is usually obtainable by polymerizing the cationic vinyl monomer (A) and the vinyl monomer (B), having structures corresponding to the respective constituting units, in the corresponding molar fractions.

Here, the vinyl monomer is a vinyl-polymerizable monomer. The cationic vinyl monomer is a vinyl monomer having at least one cationic group and having no anionic group or a less number of anionic groups than cationic groups.

Vinyl Monomer (B)

As the vinyl monomer (B), one represented by the following formula (1) or (2) is used. Otherwise, ones represented by the formulae (1) and (2) may be used in combination.

$$CH_2=C(R^1)-CO-NR^2R^3 \quad (1)$$

to wherein $R^1$ is a hydrogen atom or a methyl group, and each of $R^2$ and $R^3$ which are independent of each other, is a hydrogen atom or a $C_{1-4}$ alkyl group, provided that the sum of carbon numbers of $R^2$ and $R^3$ is from 1 to 4.

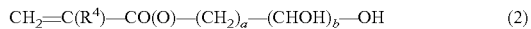
$$CH_2=C(R^4)-CO(O)-(CH_2)_a-(CHOH)_b-OH \quad (2)$$

wherein $R^4$ is a hydrogen atom or a methyl group, a is an integer of from 1 to 4, and b is 0 or 1.

Here, $R^1$ is preferably a hydrogen atom. Each of $R^2$ and $R^3$ which are independent of each other, is preferably a hydrogen atom or a $C_{1-3}$ alkyl group. The $C_{1-3}$ alkyl group may, for example, be a methyl group, an ethyl group, a propyl group or an isopropyl group. The sum of carbon numbers of $R^2$ and $R^3$ is preferably from 2 to 4, most preferably 2. a is preferably an integer of from 1 to 3, most preferably 2.

The vinyl monomer (B) of the formula (1) is not particularly limited so long as it is one contained in this formula. It may, for example, be an alkyl acrylamide such as N-methyl (meth)acrylamide, N-ethyl (meth)acrylamide, N-propyl (meth)acrylamide or N-isopropyl (meth)acrylamide; or a dialkyl acrylamide such as N,N-dimethyl (meth)acrylamide or N,N-diethyl (meth)acrylamide (here "(meth)acryl" represents acryl and methacryl).

Among them, preferred is N-methyl (meth)acrylamide, N-ethyl (meth)acrylamide, N-propyl (meth)acrylamide, N-isopropyl (meth) acrylamide, N,N-dimethyl (meth) acrylamide or N,N-diethyl (meth)acrylamide, in view of the solubility of the monomer in water and the high hydrophilicity of the copolymer thereby obtainable.

The vinyl monomer (B) of the formula (2) is not particularly limited so long as it is one contained in this formula. It may, for example, be a hydroxyalkyl (meth)acrylate such as 1-hydroxymethyl (meth)acrylate, 2-hydroxyethyl (meth) acrylate, 3-hydroxypropyl (meth)acrylate or 2,3-dihydroxypropyl (meth)acrylate. Among them, preferred is 2-hydroxyethyl (meth)acrylate or 2,3-dihydroxypropyl (meth) acrylate in view of the solubility of the monomer in water and the high hydrophilicity of the copolymer thereby obtainable.

As the vinyl monomer (B), when it has an amide bond, the adsorption on the hair, etc. will be promoted, and it is more preferred to use a vinyl monomer of the formula (1). In view of the highly silky texture and no stiffness of the hair after washing, it is further preferably one of the above formula (1) wherein the sum of carbon numbers of $R^2$ and $R^3$ is from 2 to 4. It is, for example, N,N-dimethyl (meth)acrylamide, N,N-diethyl (meth)acrylamide or N-isopropyl (meth)acrylamide. Most preferred is N,N-dimethyl (meth)acrylamide.

Further, such vinyl monomers (B) may be used alone or in combination as a mixture of two or more of them.

The vinyl monomer (B) is usually a nonionic vinyl monomer.

Cationic Vinyl Monomer (A)

The cationic vinyl monomer (A) is not particularly limited so long as it is capable of accomplishing the object of the present invention. It may, for example, be a diallyl quaternary ammonium salt such as N,N-dimethyl-N,N-diallyl ammonium chloride, a (meth)acrylester quaternary ammonium salt such as N-methacryloyloxyethyl-N,N,N-trimethylammonium chloride, a (meth) acrylamide quaternary ammonium salt such as N-methacryloylaminopropyl-N,N,N-trimethylammonium chloride or an amino acid type cationic species such as a reaction product of L-arginine with glycidyl methacrylate. Among them, (meth)acrylic quaternary ammonium salt monomer is more preferred. Particularly preferred is a (meth)acrylic quaternary ammonium salt monomer represented by the formula (3).

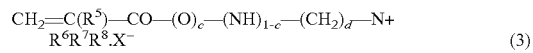
$$CH_2=C(R^5)-CO-(O)_c-(NH)_{1-c}-(CH_2)_d-N^+R^6R^7R^8.X^- \quad (3)$$

wherein $R^5$ is a hydrogen atom or a methyl group, each of $R^6$ and $R^7$ which are independent of each other, is a $C_{1-24}$ alkyl group, an aryl group or an aralkyl group, $R^8$ is a hydrogen atom, a $C_{1-24}$ alkyl group, an aryl group, an aralkyl group or $-CH_2-CH(OH)-CH_2N^+R^9R^{10}R^{11}.Y^-$, each of $R^9$ to $R^{11}$ which are independent of one another, is a $C_{1-24}$ alkyl group, an aryl group or an aralkyl group, each of $X^-$ and $Y^-$ which are independent of each other is an anion, c is 0 or 1, and d is an integer of from 1 to 10.

$R^5$ is preferably a methyl group. Each of $R^6$ and $R^7$ which are independent of each other, is preferably a methyl group or an ethyl group, more preferably a methyl group. $R^8$ is preferably a methyl group or an ethyl group, more preferably a methyl group. Each of $R^9$ to $R^{11}$ which are independent of one another is preferably a is methyl group or an ethyl group, more preferably a methyl group. The anion for $X^-$ and $Y^-$ which are independent of each other, is preferably a halogen ion, more preferably a chlorine ion, an iodine ion or a bromine ion. c is preferably 0. d is preferably an integer of from 1 to 5, more preferably 3.

The cationic vinyl monomer of the formula (3) may, for example, be a (meth)acrylic acid ester having a cationic group, such as N-(meth)acryloyloxyethyl-N,N,N-trimethylammonium chloride, N-(meth)acryloyloxyethyl-N-ethyl-N, N-dimethylammonium monoethyl sulfate, N-(meth)acryloyloxyethyl-N,N,N-triethylammonium monoethyl sulfate, N-[3-{N'-(meth)acryloyloxyethyl-N',N'-dimethylammonium}-2-hydroxyproyl]-N,N,N-trimethylammonium chloride or N-[3-{N'-(meth)acryloyloxyethyl-N'N'-diethylammonium}-2-hydroxylpropyl]-N,N,N-triethylammonium chloride; or a (meth)acrylamide having a cationic group, such as N-(meth)acryloylaminopropyl-N,N,N-trimethylammonium chloride, N-(meth)acryloylaminopropyl-N-ethyl-N,N-dimethylammonium monoethyl sulfate, N-(meth)acryloylaminopropyl-N,N-diethyl-N-methylammonium chloride, N-(meth)acryloylaminopropyl-N,N-diethyl-N-methylammonium monomethyl sulfate, N-[3-{N'-(meth)acryloylaminopropyl-N'N'-dimethylammonium}-2-hydroxypropyl]-N, N,N-trimethylammonium chloride, or N-[3-{N'-(meth) acryloylaminopropyl-N',N'-diethylammonium}-2-hydroxypropyl]-N,N,N-trimethylammonium chloride.

Among them, N-(meth)acryloyloxyethyl-N,N,N-trimethylammonium chloride or N-(meth)acryloylaminopropyl-N,N,N-trimethylammonium chloride is preferably employed, and particularly preferably N-(meth)acryloylaminopropyl-N,N,N-trimethylammonium chloride is employed. Most preferably, N-(meth)acryloyloxyethyl-N,N,N-trimethylammonium chloride and N-(meth)acryloylaminopropyl-N,N,N-trimethylammonium chloride are used in combination.

As the cationic vinyl monomer (A), it is preferred to use one having an amide bond, i.e. a monomer of the formula (3)

wherein c=0. When the copolymer has amide bonds, there will be a merit such that the adsorption to the hair will be promoted. Namely, as it has amide bonds, the cation intensity of the cationic functional groups tends to be strong, whereby the bond strength to the anionic surfactant will increase, and the adhesion strength to the hair will be high. It is thereby possible to increase the smoothness in rinsing when a detergent composition having the copolymer of the present invention incorporated, is used.

Roles of a conditioning polymer to be incorporated to a detergent composition for the hair, may, for example, be to impart smoothness in rinsing, a silky texture after drying and non-stiffness after drying. Among them, most important is the smoothness in rinsing, because it is not possible to supplement the smoothness is in rinsing by any other method, while it is possible to improve the texture after drying by carrying out treatment with a rinse or conditioner, or with an out-bath treatment agent of non-washing off type. Accordingly, as a polymer for conditioning, one excellent in the smoothness in rinsing is most preferred.

Further, the structure corresponding to the cationic vinyl monomer (A) may also be obtained by polymerizing a precursor of the cationic vinyl monomer with the vinyl monomer (B), followed by conversion to a structure having the corresponding cationic groups by a cation-forming agent.

The cationic vinyl monomer precursor may, for example, be a (meth)acrylic acid ester having a tertiary amine, such as N-(meth)acryloyloxyethyl-N,N-dimethylamine or N-(meth)acryloyloxyethyl-N,N-diethylamine; or a (meth)acrylamide having a tertiary amine, such as N-(meth) acryloylaminopropyl-N,N-dimethylamine or N-(meth)acryloylaminopropyl-N,N-diethylamine.

The cation-forming agent may, for example, be an alkyl halide such as methyl chloride, or a cation group-containing cation-forming agent such as 3-chloro-2-hydroxypropyl-N,N,N-trimethylammonium chloride. The cation forming reaction may be carried out under conditions of from 20 to 100° C. for from 1 to 20 hours by adding the cation-forming agent to the polymer solution.

Here, the cationic vinyl monomers (A) or their precursors may be used alone or in combination as a mixture of two or more of them.

Combined Use of Cationic Vinyl Monomers (A)

In one of preferred embodiments of the present invention, as the cationic vinyl monomer (A), a monomer (A1) of the above formula (3) wherein c is 1, and a monomer (A2) of the formula (3) wherein c is 0, are used in combination. It is thereby possible to obtain a merit such that when they are incorporated to a detergent composition, the effects such as the smoothness in rinsing, the smooth finger-combing after towel-dry and the silky texture, non-stiffness and flexibility after drying will be further improved with respect to the skin or hair, particularly not only for non-treated hair but also for damaged hair.

The reason for such further improvement in effects by the combined use of monomers (A1) and (A2) is not clearly understood. However, it is considered that as the vinyl monomer (A2) has an amide bond, it has an effect to have the complex with the surfactant component readily adsorbed by the skin or hair by a hydrogen bond action with the skin or hair surface. On the other hand, as the copolymer contains constituting units corresponding to the vinyl monomer (A1) having an ester bond, the state after deposition of the complex on the hair tends to be hydrophobic and tends to be a state close to healthy hair, whereby the effect to improve the texture of the hair, etc. tends to be high. Thus, by the combined use of the polymers (A1) and (A2), the characteristics of the two are believed to be obtainable.

Preferably, the proportion of constituting units corresponding to the monomer (A1) in the entire constituting units constituting the copolymer is from 1 to 44 mol %, the proportion of constituting units corresponding to the monomer (A2) is from 1 to 44 mol %, and the total of the proportions of the two is from 25 to 45 mol %.

The proportion of the constituting units corresponding to the vinyl monomer (A1) in the entire constituting units constituting the copolymer is at least 1 mol %, whereby the copolymer contains cationic groups in a sufficient amount, so that it tends to readily form a complex with a surfactant component to increase the amount of adsorption on the hair thereby to increase the effect such as the silky texture after drying. Such a proportion is more preferably at least 3 mol %, further preferably at least 5 mol %, most preferably at least 10 mol %.

However, the proportion of the constituting units corresponding to the cationic vinyl monomer (A1) in the entire constituting units constituting the copolymer is at most 44 mol %, whereby the complex with the surfactant tends to be readily re-dispersed to readily obtain a uniform solution. Such a proportion is more preferably at most 40 mol %, further preferably at most 30 mol %.

The proportion of the constituting units corresponding to the vinyl monomer (A2) in the entire constituting units constituting the copolymer is at least 1 mol %, whereby the copolymer contains cationic groups in a sufficient amount, and it tends to readily form a complex with a surfactant component to increase the amount of adsorption to the hair thereby to increase the effect such as the silky texture after drying. Such a proportion is more preferably at least 3 mol %, further preferably at least 5 mol %, most preferably at least 10 mol %.

The proportion of the constituting units corresponding to the cationic vinyl monomer (A2) in the entire constituting units constituting the copolymer, is at most 44 mol %, whereby the complex with the surfactant tends to be readily re-dispersed thereby to readily obtain a uniform solution. Such a proportion is more preferably at most 40 mol %, further preferably at most 30 mol %.

The total of the proportions of the constituting units corresponding to the vinyl monomers (A1) and (A2) in the entire constituting units constituting the copolymer is from 25 to 45 mol %, more preferably from 30 to 40 mol %. By adjusting the total amount to be at least 25 mol %, the copolymer will contain cationic groups in a sufficient amount, whereby the complex with the surfactant component tends to be easily formed, the amount of adsorption on the hair increases, and for example, the effect such as the silky texture after drying will be improved. On the other hand, by adjusting the total to be at most 45 mol %, the complex with the surfactant tends to be readily re-dispersed, whereby a uniform solution tends to be readily obtainable.

Other Monomers

In the copolymer, structural units derived from other vinyl monomers may further be contained. However, if anionic functional groups are present in the copolymer, they may hinder formation of a complex with the above-mentioned anionic surfactant. Accordingly, one containing a small amount of anionic functional groups (e.g. at most 10% of the entire functional groups), is preferred, and one not substantially containing such anionic functional groups, is more preferred. Here, not substantially containing is meant for e.g. one showing no anionic property at pH 3 to 8.

Such other vinyl monomers may, for example, be an ester of a $C_{1-22}$ alcohol with (meth)acrylic acid; an amide of a $C_{1-22}$ alkylamine with (meth)acrylic acid; a monoester of ethylene glycol, 1,3-propylene glycol or the like with (meth)acrylic acid; an ester having a hydroxyl group or the above-mentioned monoester etherified with methanol, ethanol or the like; a nonionic monomer such as (meth)acryloyl morpholine, hydroxymethylacrylamide or hydroxyethylacrylamide; an amphoteric monomer such as a betaine group-containing (meth)acrylic ester or a betaine group-containing (meth)acrylamide; or a semi-polar monomer such as an amine oxide group-containing (meth)acrylic ester or an amine oxide group-containing (meth) acrylamide.

The content of structural units derived from such other vinyl monomers may optionally be determined within a range not to depart from the concept of the present invention. For example, it may optionally be determined within a range not to impair e.g. the solubility of the copolymer, the conditioning effect when the copolymer is used for a hair cosmetic, etc. Accordingly, the content of such structural units is preferably at most 30 wt %, more preferably at most 20 wt %, in the copolymer.

The contents of the constituting units corresponding to the cationic vinyl monomer (A), the constituting units corresponding to the vinyl monomer (B) having a hydroxyl group and an amide bond, and the constituting units derived from other vinyl monomers, in the copolymer, may be measured by the IR absorption of the hydroxyl group or amide bond moiety; $^{1}$H-NMR of the hydroxyl group or amide bond moiety, or the methyl group adjacent to a cationic group; or their $^{13}$C-NMR.

The copolymer of the present invention is preferably one capable of forming an aqueous solution having a concentration of at least 5 wt % at room temperature i.e. at 25° C., namely one whereby the transmittance (550 nm) of the aqueous solution having a concentration of at least 5 wt % is at least 80%, and the aqueous solution is uniform and stable. More preferably, the copolymer is one capable of forming an aqueous solution having a concentration of at least 20 wt %.

Copolymer and Process for its Production

The copolymer of the present invention may be produced, for example, by mixing monomers to present the respective constituting units or their precursors, copolymerizing them by a method such as solution polymerization, suspension polymerization or emulsion polymerization, and then carrying out a cation-forming reaction, as the case requires.

The polymerization reaction is preferably carried out in a hydrophilic solvent. The hydrophilic solvent may, for example, be a ketone solvent such as acetone, methyl ethyl ketone or methyl isobutyl ketone; an alcohol solvent such as methanol, ethanol, n-propanol, propanol, n-butanol, i-butanol or sec-butanol; or water. These solvents may be used alone or in combination as a mixture of two or more of them. It is preferred to use an alcohol solvent or water.

As a polymerization initiator, an azo compound such as 2,2'-azobisisobutyronitrile, 2,2'-azobis(2,4-dimethylvaleronitrile), 2,2'-azobis(4-methoxy-2,4-dimethylvaleronitrile), dimethyl-2,2'-azobisisobutyrate, 2,2'-azobis(2-methylbutyronitrile), 1,1'-azobis(1-cyclohexanecarbonitrile), 2,2'-azobis(2-methyl-N-(2-hydroxyethyl)-propionamide) or 2,2'-azobis(2-amidinopropane)dihydrochloride; a peroxide such as benzoyl peroxide, dicumyl peroxide, di-t-butyl peroxide or lauroyl peroxide, or a persulfate or its redox initiator may, for example, be used without any particular restriction. The polymerization initiator is used preferably within a range of from 0.01 to 5 wt %, more preferably within a range of from 0.1 to 3 wt %, based on the total monomers.

The polymerization reaction may be carried out, for example, in an atmosphere of an inert gas such as nitrogen or carbon, preferably at a temperature of from 30 to 120, more preferably from 40 to 100° C. usually for from 1 to 30 hours. After completion of the polymerization, the formed copolymer may be isolated from the reaction solution by a suitable means such as distillation of the solvent or addition of a poor solvent. The copolymer may be used as it is or after purification for the production of e.g. a hair cosmetic of the present invention. The purification may be carried out by suitable means such as reprecipitation, washing with a solvent and separation by a membrane, if necessary in combination.

As the copolymer of the present invention, one having an optional structure, such as a random copolymer, a block copolymer or a graft copolymer, may be used without any particular restriction.

The random copolymer may be prepared by a method wherein an initiator is added in a state where all monomers to be used for the polymerization are mixed to carry out the reaction all at once, or a method wherein part or the entire amount of monomers is dropwise added so that the reaction is gradually carried out. Further, it is also possible to carry out the polymerization by dropwise addition while the monomer composition is changed.

The block copolymer may be prepared by using a known radical initiator or catalyst.

The graft copolymer may be prepared by a method of using a macromer having a vinyl type functional group or by a method of reacting polymers having reactive functional groups to each other.

Among them, one capable of being prepared from inexpensive starting materials without requiring any special step is preferred as the industrial application value is high, and a random copolymer which can be prepared most simply by using usual starting materials, is most preferred.

Further, at the time of incorporating the copolymer of the present invention to a detergent composition, a plurality of copolymers may be used in combination. In such a case, the copolymers may be separately prepared and then mixed and incorporated. Otherwise, firstly, one copolymer is produced, and in its reaction solution, a monomer component to constitute another copolymer may be added and polymerized, to obtain a mixture of two copolymers. By repeating the addition and polymerization of a monomer component in such a manner, it is possible to obtain a mixture of a larger number of copolymers. In the present invention, the latter method is preferred since the copolymer can thereby be simply produced.

The weight average molecular weight of the copolymer of the present invention is preferably from 10,000 to 2,000,000. By adjusting the weight average molecular weight to be at least 10,000, it is possible to increase the conditioning effect by deposition of the complex with the anionic surfactant on the hair or skin. The weight average molecular weight is more preferably at least 100,000, further preferably at least 200,000. On the other hand, by adjusting it to be at most 2,000,000, the viscosity can be maintained properly, the blending efficiency will be high, and handling efficiency for the production will also be high. The weight average molecular weight is more preferably at most 1,000,000, further preferably at most 700,000. The weight average molecular weight of the copolymer may be measured by gel permeation chromatography (using e.g. water/methanol/acetic acid/sodium acetate as a developing solvent).

In the present invention, the viscosity of the solution is preferably within a proper range, for example, at a level where a 20 wt % aqueous solution of the copolymer can be prepared.

The viscosity of the 20 wt % aqueous solution at 25° C. is preferably at most 100,000 mPa·s, more preferably at most 50,000 mPa·s, further preferably at most 20,000 mPa·s, most preferably at most 5,000 mPa·s. However, such a viscosity is usually at least 10 mPa·s. A high concentration is preferred, since the transportation will thereby be easy.

Adjustment of the viscosity may be carried out, for example, by controlling the polymerization degree of the copolymer. Further, the molecular weight and viscosity can be controlled by adjusting the amount of a cross-linking agent such as a polyfunctional acrylate. However, if the cross-linking agent is added too much even slightly, the molecular weight and viscosity are likely to sharply increase, thus leading to difficulty in control for industrial production. If the molecular weight and viscosity become too large, the blending efficiency tends to decrease as mentioned above, such being undesirable. Accordingly, it is preferred that the amount of the cross-linking agent is within the range not to increase the molecular weight by the polymerization. For example, it is preferably at most 0.1%, more preferably at most 0.01%, based on the amount of the copolymer. Most preferably, no cross-linking agent is employed for the polymerization of the copolymer, so that no cross-linking agent is contained as a constituting component of the copolymer.

As a method for controlling the molecular weight of the copolymer, a method of using a chain transfer agent may also be mentioned. By adding a chain transfer agent, it is possible to reduce the molecular weight. However, if the amount of its addition is too much, the molecular weight tends to be too small, thus leading to a difficulty in control for industrial production. Further, a thiol such as thioglycol, an alkylthiol or thioglycolic acid, which is commonly used as a chain transfer agent, has a demerit of causing deterioration in the odor. Therefore, it is preferred that no chain transfer agent is incorporated.

Detergent Composition

The detergent composition of the present invention may be prepared by blending at least one type of the above copolymer and at least one type of a surfactant in prescribed amounts in a formulation system.

The above copolymer exhibits excellent conditioning effects when incorporated to such a detergent composition, and the detergent composition containing such a copolymer presents excellent effects such as smoothness and smooth finger-combing in rinsing, and a silky texture and flexibility after drying, to the skin or hair, particularly not only to non-treated hair but also to damaged hair.

The concentration of the copolymer in the detergent composition is preferably from 0.01 to 5 wt %. By adjusting the concentration of the copolymer to be at least 0.01 wt %, its complex with a surfactant tends to be readily formed, and the conditioning effects will be developed more efficiently, whereby the smoothness in rinsing or the silky texture after drying will further be improved. The concentration of the copolymer is more preferably at least 0.05 wt %, further preferably at least 0.1 wt %. On the other hand, by adjusting the concentration of the copolymer in the detergent composition to be at most 5 wt %, an uncomfortable feeling after drying tends to be less. The concentration of the copolymer is more preferably at most 3 wt %, further preferably at most 1 wt %.

The surfactant is not particularly limited, and it may, for example, be an anionic surfactant, an amphoteric surfactant, a nonionic surfactant or a semi-polar surfactant. Other components may be incorporated to the detergent composition, as the case requires. Such other components are not particularly limited and may be incorporated within a range not to impair the purpose or the effects of the present invention. Specifically, they may, for example, be a water-soluble polymer, a cationic polymer, an anionic polymer, a nonionic polymer, an amphoteric polymer, an oil component and a pearling agent, other than the copolymer of the present invention.

Combined Use of Plural Copolymers Different in the Proportion of Cationic Monomer One of preferred embodiments of the detergent composition of the present invention is a detergent composition which contains, as the copolymer, at least a copolymer (C1) and a copolymer (C2), wherein the proportion of constituting units corresponding to the cationic vinyl monomer (A) in the entire constituting units constituting the copolymer (C2) is larger than the proportion of constituting units corresponding to the cationic vinyl monomer (A) in the entire constituting units constituting the copolymer (C1).

Namely, each of the copolymers (C1) and (C2) comprises constituting units corresponding to the cationic vinyl monomer and constituting units corresponding to the vinyl monomer having a specific structure, and the proportion of the constituting units corresponding to the cationic vinyl monomer in the entire constituting units constituting the copolymer (C2) is larger than the proportion of the constituting units corresponding to the cationic vinyl monomer in the entire constituting units constituting the copolymer (C1). According to this embodiment, the detergent composition will have a merit such that the effects such as the smoothness and smooth finger-combing in rinsing, and the silky texture and flexibility after drying, will be improved with respect to the skin or hair, particularly with respect to not only non-treated hair but also damaged hair.

The reason for such improvement in effects by the combined use of copolymers different in the cationic degree is not clearly understood. However, it is considered that the copolymer (C2) having many constituting units corresponding to the cationic vinyl monomer has a high cationic degree and thus has a high effect to let the complex with the surfactant readily deposit on the hair, etc., while the copolymer (C1) having less constituting units corresponding to the cationic vinyl monomer has a relatively low cationic degree and thus has a high effect to improve the texture of the hair, etc. having the complex deposited thereon, and thus the characteristics of both will be readily obtainable by the combined use.

The proportion of constituting units corresponding to the cationic vinyl monomer in the entire constituting units constituting the copolymer (C2) is larger than the proportion of constituting units corresponding to the cationic vinyl monomer in the entire constituting units constituting the copolymer (C1). The copolymer thereby contains cationic groups in a sufficient amount and tends to readily form a complex with the surfactant component, and the amount of adsorption on the hair will increase. Such a proportion is preferably at least 27 mol %, more preferably at least 30 mol %. However, the proportion is at most 45 mol %.

The proportion of constituting units corresponding to the cationic vinyl monomer in the entire constituting units constituting the copolymer (C1) is preferably at most 42 mol %. The complex with the surfactant thereby tends to be readily re-dispersible, and a uniform solution tends to be easily obtainable. However, such a proportion is at least 25 mol %. The proportion is more preferably at most 38 mol %, further preferably at most 35 mol %.

The difference in the proportion of the cationic vinyl monomer between the copolymers (C1) and (C2) may usually be at least 1 mol %, but is preferably at least 3 mol % and at most 20 mol %.

Further, in each of the copolymers (C1) and (C2), the proportion of constituting units corresponding to the vinyl monomer of the formula (1) or (2) in the constituting units of the copolymer other than the constituting units corresponding to the above-mentioned cationic vinyl monomer is preferably from 30 to 100 mol %. By adjusting the proportion to be at least 30 mol %, a sufficient water-solubility tends to be easily obtainable, and the complex with the surfactant tends to be readily re-dispersible and a uniform solution tends to be readily obtainable. Further, the smoothness in rinsing or the silky texture after drying may, for example, be maintained more effectively. Such a proportion is more preferably from 50 to 100 mol %, further preferably from 70 to 100 mol %.

Further, the vinyl monomers to be used for the copolymers (C1) and (C2) may be the same or different.

In the detergent composition, the ratio of the copolymers (C1) and (C2) is preferably such that the weight ratio of the copolymer (C1) based on the sum of the weights of the copolymers (C1) and (C2) i.e. $\{(C1)/((C1)+(C2))\times 100\}$, is from 1 to 99 wt %. In order to sufficiently obtain the effect to improve the texture of the one deposited on the hair, etc. which is a characteristics of the copolymer (C1), the weight ratio is preferably at least 1 wt %, more preferably at least 20 wt %, further preferably at least 40 wt %, most preferably at least 50 wt %.

Further, in order to sufficiently obtain the effect for adsorption on the hair, etc. which is a characteristic of the copolymer (C2), such a weight ratio is at most 99 wt %, more preferably at most 95 wt %, further preferably at most 80 wt %, most preferably at most 75 wt %.

Combined Use of Plural Copolymers Different in Type of Cationic Monomer

Another preferred embodiment of the detergent composition of the present invention is a detergent composition which contains, as the copolymer, at least a copolymer (C3) and a copolymer (C4), wherein the copolymer (C3) is a copolymer comprising constituting units corresponding to a vinyl monomer of the formula (1) or (2) and constituting units corresponding to a monomer (A1) of the formula (3) wherein c is 1, and the copolymer (C4) is a copolymer comprising constituting units corresponding to a vinyl monomer of the formula (1) or (2) and constituting units corresponding to a monomer (A2) of the formula (3) wherein c is 0.

Namely, the detergent composition of the present invention comprises the copolymer (C3) comprising constituting units corresponding to the vinyl monomer having a specific structure containing an amide bond or a hydroxyl group and a vinyl monomer having a specific structure containing an ester bond, and the copolymer (C4) comprising constituting units corresponding to a vinyl monomer having a specific structure containing an amide bond or a hydroxyl group and a vinyl monomer having a specific structure containing an amide bond. This embodiment provides a merit of improving the effects of the detergent composition such as the smooth finger-combing in rinsing, and the silky texture and flexibility after drying, given to the skin or hair, particularly not only to non-treated hair but also to damaged hair.

The reason for such improvement in effects by the combined use of two different types of copolymers, is not clearly understood. However, it is considered that the copolymer (C4) has amide bonds and thus has an effect to let the above complex be readily adsorbed on the skin or hair by the hydrogen bond action with the skin or hair surface, and the copolymer (C3) has ester bonds, whereby the state after the deposition of the complex on the hair tends to be hydrophobic and close to the state of healthy hair thereby to increase the effect to improve the texture of the hair, etc. Thus, it is considered that by the combined use of the copolymers (C3) and (C4), the characteristics of the two can be obtained.

The proportion of the constituting units corresponding to the vinyl monomer of the formula (3) in the entire constituting units constituting the copolymer (C3) is preferably at least 27 mol %. The copolymer thereby contains cationic groups in a relatively large amount and tends to readily form a complex with the surfactant component, whereby the amount of adsorption on the hair will increase, thereby to increase the effect such as the silky texture, etc. after drying. However, such a proportion is preferably at most 42 mol %, particularly preferably at most 38 mol %. The complex with the surfactant thereby tends to be readily re-dispersible, and a uniform solution tends to be readily obtainable.

The proportion of the constituting units corresponding to the vinyl monomer of the formula (3) in the entire constituting units constituting the copolymer is (C4) is the same as in the copolymer (C3).

Further, in each of the copolymers (C3) and (C4), the proportion of the constituting units corresponding to the vinyl monomer of the formula (1) or (2) in the constituting units of the copolymer other than the constituting units corresponding to the above-mentioned cationic vinyl monomer is preferably from 30 to 100 mol %. By adjusting the proportion to be at least 30 mol %, a sufficient water-solubility tends to be readily obtainable, and the complex with the surfactant tends to be readily re-dispersible, and a uniform solution tends to be readily obtainable. Further, the smoothness in rinsing, the silky texture after drying, etc., tend to be maintained more effectively. Such a proportion is more preferably from 50 to 100 mol %, further preferably from 70 to 100 mol %.

Further, for the copolymers (C3) and (C4), the vinyl monomers to be used other than the vinyl monomer of the formula (3) may be the same or different.

In the detergent composition, the ratio of the copolymers (C3) and (C4) is preferably such that the weight ratio of the copolymer (C3) to the sum of the weights of the copolymers (C3) and (C4) i.e. $\{(C3)/((C3)+(C4))\times 100\}$ is from 1 to 99 wt %. In order to obtain a sufficient effect to improve the texture by making the hair, etc. to be hydrophobic, as a characteristic of the copolymer (C), such a ratio is preferably at least 1 wt %, more preferably at least 20 wt %, further preferably at least 40 wt %.

Further, in order to obtain a sufficient effect for adsorption on the hair, etc., as the characteristic of the copolymer (C4), the above ratio is preferably at most 99 wt %, more preferably at most 90 wt %, further preferably at most 80 wt %.

Surfactant

The detergent composition contains at least one surfactant. Particularly preferably, it contains at least an anionic surfactant, whereby a complex can readily be formed with the copolymer having cationic groups of the present invention. As such an anionic surfactant, one commonly used for detergent compositions may be used, such as an α-olefin sulfonate, a higher alcohol sulfuric acid ester, a polyoxyethylene alkyl ether sulfuric acid ester, a paraffin sulfonate, a polyoxyethylene alkyl ether carboxylic acid ester, an alkyl sulfosuccinate, an N-acyl-β-alanine salt, an N-acyl glutamic acid salt or an acyl methyl taurine salt. As a counter ion for such an anionic surfactant, sodium, potassium, ammonium, triethanolamine or diethanolamine to may, for example, be mentioned. Further, such anionic surfactants may be used in combination as a mixture of two or more of them.

The concentration of the anionic surfactant is preferably from 5 to 40 wt %, more preferably from 10 to 30 wt %. Further, the concentration of the copolymer is preferably from 0.01 to 5 wt %, more preferably from 0.05 to 3 wt %. By adjusting the anionic surfactant and the copolymer within the above concentration ranges, a complex of the anionic surfactant and the copolymer will be formed in the obtained detergent composition, and at the time of washing or rinsing the hair, this complex will precipitate and deposit on the hair to present the smooth finger-combing.

By adjusting the concentration of the anionic surfactant to be at least 5 wt %, the function as a detergent composition can more effectively be provided. The concentration is more preferably at least 10 wt %. On the other hand, by adjusting the concentration to be at most 40 wt %, the viscosity can be maintained to be proper, whereby the handling will be easy. Such a concentration is more preferably at most 30 wt %.

Other surfactants which may be incorporated to the detergent composition will be exemplified below.

The amphoteric surfactant may, for example, be one having a betaine group and a long chain alkyl group, such as aminoacetic acid betaine, imidazolium betaine, sulfobetaine or amidopropyl betaine. Such an amphoteric surfactant is commercially available and may be used as it is. Among them, a long chain alkyl amidopropyl betaine is preferably used from the viewpoint of foaming and cleaning properties. The concentration of the amphoteric surfactant is usually from 0 to 10 wt %.

The nonionic surfactant may, for example, be a polyoxyethylene hardened castor oil, a polyoxyethylene alkyl ether, a fatty acid monoethanol amide or a fatty acid diethanol amide. Such a nonionic surfactant is commercially available and may be used as it is. Among them, a fatty acid monoethanol amide or a fatty acid diethanol amide is preferably employed from the viewpoint of e.g. foaming and the nature suitable as a viscosity-adjusting agent. The concentration of the nonionic surfactant is usually from 0 to 10 wt %.

The semi-polar surfactant may, for example, be lauramine oxide (lauryl dimethylamine oxide). The concentration of the semi-polar surfactant is usually from 0 to 10 wt %.

A particularly preferred detergent composition is one comprising from 5 to 40 wt % of an anionic surfactant, from 0.01 to 5 wt % of the copolymer, and from 0 to 10 wt % in total of at least one surfactant selected from the group consisting of an amphoteric surfactant, a nonionic surfactant and a semi-polar surfactant, and such a detergent composition will exhibit excellent effects as a detergent composition for the hair, such as a shampoo.

In such a case, the amphoteric surfactant, the nonionic surfactant and the semi-polar surfactant may be in a total amount of from 0 to 10 wt %, and one of them may be used, or two or more of them may be used in combination.

Other Blend Components

Other optional components which may be incorporated to the detergent composition will be exemplified below.

As a cationic polymer, a cation-modified cellulose ester derivative, a polydimethyl diallyl ammonium halide, or a copolymer of a dimethyl diallyl ammonium halide with an acrylamide may, for example, be mentioned.

Further, as an anionic polymer, an acrylic acid derivative (such as a polyacrylic acid or its salt, an acrylic acid/acrylamide/ethyl copolymer or its salt), a methacrylic acid derivative or a crotonic acid derivative, may, for example, be mentioned.

As a nonionic polymer, an acrylic acid derivative (such as a hydroxyethyl acrylate/methoxyethyl acrylate copolymer, or a polyacrylamide), a vinyl pyrrolidone derivative (such as polyvinyl pyrrolidone or a vinyl pyrrolidone/vinyl acetate copolymer) may, for example, be mentioned.

As an amphoteric polymer, a dimethyl diallyl ammonium chloride derivative (such as an acrylamide/acrylic acid/dimethyl allyl ammonium chloride copolymer or an acrylic acid/dimethyl diallyl ammonium chloride copolymer) may, for example, be mentioned.

These polymers may be incorporated preferably in an amount of from 0.1 to 1 wt %.

As an oil component, a higher alcohol, silicone oil, olive oil, jojoba oil, liquid paraffin or a fatty acid alkyl ester oil may, for example, be mentioned. Among them, silicone oil and/or a higher alcohol is particularly effective for the purpose of the present invention, since when it is incorporated, the silky texture after drying will be improved. As such silicone oil, a non-volatile polydimethylsiloxane may preferably be used. The higher alcohol is usually meant for an alcohol having at least 8 carbon atoms, and it is preferred to use a $C_{8-22}$ alcohol. Among them, it is particularly preferred to use cetyl alcohol (cetanol) or stearyl alcohol. The oil component is preferably incorporated in an amount of from 0.1 to 3 wt %.

As a pearling agent, a fatty acid ethylene glycol such as distearic acid ethylene glycol may, for example, be mentioned. The pearling agent is preferably incorporated in an amount of from 0.1 to 2 wt %.

As a suspending agent, a polystyrene emulsified product may, for example, be mentioned.

As other components, a natural extract of a plant or animal or its derivative; an organic acid such as citric acid or lactic acid; an inorganic salt such as sodium chloride; a solubilizing agent (such as ethanol, ethylene glycol or propylene glycol), a moisturizer (such as glycerol, sorbitol, multitol, dipropylene glycol, 1,3-butylene glycol or hyaluronic acid), an antioxidant, an ultraviolet absorber, a fungicide, an antiseptic, a chelating agent, a perfume, a colorant, a higher fatty acid, a thickener, a metal-sealing agent (such as an edetate), a pH-controlling agent, and a foaming accelerator, may, for example, be suitably incorporated within a range not to impair the effects of the present invention.

EXAMPLES

Now, the present invention will be described in further detail with reference to Examples. However, it should be understood that the present invention is by no means restricted by the following Examples.

Analysis and Evaluation Method (1) Measurement of Weight Average Molecular Weight of Copolymer By means of gel permeation chromatography (apparatus: SC8010, SD8022, RI8020, CO8011, PS8010, manufactured by TOSOH CORPORATION, column: Wakopak (Wakobeads G-50), manufactured by Wako Pure Chemical Industries, Ltd., developing solvent: water/methanol/acetic acid/sodium acetate=6/4/0.3/0.41), the weight average molecular weight was obtained by using polyethylene glycol as a standard substance.

Measurement of the viscosity was carried out by means of a B-type viscometer at 30 rpm at 25° C. by using rotor No. 2.

(2) Evaluation of Shampoo Compositions

Each shampoo composition was applied to a hair bundle prepared, and evaluation was made with respect to each item. Here, the hair bundle used was such that as "human black hair (100%) bundle (non-treated hair: 10 g×30 cm)", a commercial product manufactured by Beaulax was used as "non-treated hair", and one obtained by subjecting the "non-treated hair" to bleaching was used as "damaged hair". For the preparation of the damaged hair, as bleaching agents, Promatiz Flaeve occitane 6.0 (cream containing 6% of hydrogen peroxide), manufactured by Milbon and Power Bleach MR2, manufactured by Meros Chemical Co., Ltd. were used, and a mixture of 12 g and 6 g, respectively, was applied to one hair bundle. After the application, the hair bundle was left to stand for 30 minutes and then washed with water, and lauroyl (EO) 3 sodium sulfate (polyoxyethylene (3) lauryl ether sodium sulfate) was applied, followed by washing.

With respect to each group of Examples, evaluation was carried out by using a different comparative standard product.
Blending Property The transmittance of each shampoo composition was evaluated by the following three grades. However, with respect to the shampoo containing silicone oil, the transparency before addition of the silicone oil was evaluated.

0: A shampoo transparent in the same level as a comparative standard product is obtainable.

−1: A uniform shampoo is obtainable although the transparency is low.

−2: Turbidified and no shampoo is obtainable.
Smoothness in Rinsing

After treating a hair bundle with each shampoo composition, the hair bundle was rinsed in running water at 40° C., whereby the smoothness in finger-combing and the retention of such smoothness was evaluated by the following four grades.

+2: Superior in both the smoothness and its retention to a comparative standard product.

+1: Superior in either the smoothness or its retention to a comparative standard product.

0: In the same level as a comparative standard product.

−1: Inferior to a comparative standard product.
Finger-combing after towel-Dry

A hair bundle after rinsing was gently pressed by a towel to remove water, whereupon the smoothness in finger-combing was evaluated by the following four grades.

+2: Substantially superior in the silky texture to a comparative standard product.

+1: Superior in the silky texture to a comparative standard product.

0: In the same level as a comparative standard product.

−1: Inferior to a comparative standard product.
Silky Texture after Drying

The hair bundle after the evaluation of the finger-combing after towel-dry was dried in a constant temperature room at 23° C. under a relative humidity of 60% overnight, and then the silky texture of the hair bundle was evaluated by the following four grades.

+2: Substantially superior in the silky texture to a comparative standard product.

+1: Superior in the silky texture to a comparative standard product.

0: In the same level as a comparative standard product.

−1: Inferior to a comparative standard product.
Non-Stiffness after Drying

With respect to the hair bundle used for the evaluation of the silky texture, non-stiffness was evaluated by the following four grades.

+2: No substantial stiffness is felt as compared with a comparative standard product.

+1: Slight stiffness is felt although it is less than a comparative standard product.

0: In the same level as a comparative standard product.

−1: Inferior to a comparative standard product.
Abbreviations of Monomers, Etc.

DMC: N-methacryloyloxyethyl-N,N,N-trimethylammonium chloride

DMAPAAC: N-acryloylaminopropyl-N,N,N-trimethylammonium chloride

HEA: hydroxyethyl acrylate

HEMA: hydroxyethyl methacrylate

DMAA: N,N-dimethylacrylamide

DEAA: N,N-diethylacrylamide

JR400: cationic hydroxyethyl cellulose (manufactured by UCC)

Example 1-1

Preparation of Copolymer

Into a reactor equipped with a reflux condenser, a dropping funnel, a thermometer, a nitrogen gas supply tube and a stirrer, 200 parts by weight of distilled water was charged, and into the dropping funnel, a monomer mixed liquid comprising 43 parts by weight of N-methacryloyloxyethyl-N,N,N-trimethylammonium chloride (DMC) (54 parts by weight as a 80 wt % aqueous solution), 57 parts by weight of hydroxyethyl acrylate (HEA) and 80 parts by weight of distilled water, was charged. The reactor was flushed with nitrogen and then heated to 90° C. To the reactor, 0.5 part by weight of 2,2'-azobis(2-methyl-N-(2-hydroxyethyl)-propionamide was introduced, and then, the monomer mixture was dropwise added over a period of 4 hours. After completion of the dropwise addition, the reaction was carried out for 20 hours, followed by cooling to obtain a copolymer (1-1).

Of the obtained copolymer, the proportions of constituting units corresponding to the respective monomers in the entire constituting units, are DMC/HEA=30/70 (mol percent). The weight average molecular weight was 230,000, and the viscosity of a 20 wt % aqueous solution was 110 mPa·s. The results are shown in Table 1-1.
Preparation of Detergent Composition Using the copolymer (1-1) obtained by the above-described method, a shampoo having the composition shown in Table 1-2 was prepared. The numerical values in the Table are all mass amounts (parts by weight) of active ingredients.
Evaluation of Detergent Composition Using the shampoo prepared by the above-mentioned method, the blending property was evaluated by the above-mentioned method. Further, with respect to the non-treated hair and the damaged hair, the smoothness in rinsing, the silky texture after drying and the non-stiffness after drying were evaluated. The results are shown in Table 1-3.

Examples 1-2 to 1-7

Preparation of Copolymers

Copolymers (1-2) to (1-7) were prepared in the same manner as the preparation of the copolymer (1-1) except that the monomer compositions shown in Table 1-1 (copolymers (1-2) to (1-7)) were used. Of the obtained copolymers, the mol percents of the constituting units corresponding to the respective monomers in the entire constituting units, the weight average molecular weights and the viscosities of the 20% aqueous solutions are shown in Table 1-1.

Preparation and Evaluation of Detergent Compositions

By using the obtained copolymers, preparation and evaluation of shampoos having the compositions shown in Table 1-2 were carried out in the same manner as in Example 1-1. The results are shown in Table 1-3.

TABLE 1-1

| | Monomer composition (mass parts/mol percent) | | | | | | Weight average molecular weight *2 | Viscosity of 20% aqueous solution (mPa·s) |
|---|---|---|---|---|---|---|---|---|
| | Monomer (A) | | Monomer (B) | | | | | |
| | DMC | DMAPAAC | HEA | HEMA | DMAA | DEAA | | |
| Copolymer (1-1) | 43/30 | | 57/70 | | | | 230 k | 110 |
| Copolymer (1-2) | 47/30 | | | | 53/70 | | 330 k | 850 |
| Copolymer (1-3) | | 41/30 | 59/70 | | | | 230 k | 440 |
| Copolymer (1-4) | | 47/30 | | | 53/70 | | 430 k | 1,490 |
| Copolymer (1-5) | | 41/30 | | | | 59/70 | 340 k | 900 |
| Copolymer (1-6) | 58/40 | | | | 42/60 | | 300 k | 890 |
| Copolymer (1-7) | 29/20 | 29/20 | | | 42/60 | | 360 k | 970 |
| Copolymer (1-8) | 34/20 | | | | 66/80 | | 350 k | 1,130 |
| Copolymer (1-9) | 68/50 | | | | 32/50 | | 280 k | 300 |

*1: Numerical values in Table all represent mass as solid contents.
*2: k represents 1,000.

TABLE 1-2

| | Example | | | | | | | | | | Comparative Example | | |
|---|---|---|---|---|---|---|---|---|---|---|---|---|---|
| Formulation | 1-1 | 1-2 | 1-3 | 1-4 | 1-5 | 1-6 | 1-7 | 1-8 | 1-9 | 1-10 | 1-1 | 1-2 | 1-3 |
| Copolymer (1-1) | 0.5 | | | | | | | | | | | | |
| Copolymer (1-2) | | 0.5 | | | | | | 0.5 | 0.5 | 0.5 | | | |
| Copolymer (1-3) | | | 0.5 | | | | | | | | | | |
| Copolymer (1-4) | | | | 0.5 | | | | | | | | | |
| Copolymer (1-5) | | | | | 0.5 | | | | | | | | |
| Copolymer (1-6) | | | | | | 0.5 | | | | | | | |
| Copolymer (1-7) | | | | | | | 0.5 | | | | | | |
| Copolymer (1-8) | | | | | | | | | | | | 0.5 | |
| Copolymer (1-9) | | | | | | | | | | | | | 0.5 |
| JR400 | | | | | | | | | | | 0.5 | | |
| Anionic surfactant *2 | 10 | 10 | 10 | 10 | 10 | 10 | 10 | 10 | 10 | 10 | 10 | 10 | 10 |
| Amphoteric surfactant *3 | 4 | 4 | 4 | 4 | 4 | 4 | 4 | 4 | 4 | 4 | 4 | 4 | 4 |
| Nonionic surfactant *4 | 0.7 | 0.7 | 0.7 | 0.7 | 0.7 | 0.7 | 0.7 | 0.7 | 0.7 | 0.7 | 0.7 | 0.7 | 0.7 |
| Semi-polar surfactant *5 | 0.7 | 0.7 | 0.7 | 0.7 | 0.7 | 0.7 | 0.7 | 0.7 | 0.7 | 0.7 | 0.7 | 0.7 | 0.7 |
| Cetanol | | | | | | | | 1 | | 1 | | | |
| Silicone oil *6 | | | | | | | | | 1 | 1 | | | |
| Distilled water | Rest | Rest | Rest | Rest | Rest | Rest | Rest | Rest | Rest | Rest | Rest | Rest | Rest |

*1: Numerical values in Table all represent mass as solid contents.
*2: Polyoxyethylene (3) lauryl ether sodium sulfate
*3: Lauramide propyl betaine
*4: Lauric acid diethanol amide
*5: Lauramine oxide
*6: Silicone emulsion BY22029 (50 mass % aqueous solution, manufactured by Dow Corning Toray)

Examples 1-8 to 1-10

Using copolymer (1-2), shampoos having the compositions shown in Table 1-2 were prepared and evaluated in the same manner as in Example 1-1. However, in the case where silicone oil was contained, the preparation was carried out firstly by mixing other than the silicone oil and then blending silicone oil to the mixture. The results are shown in Tables 1-2 and 1-3.

Comparative Example 1-1

Using JR400 instead of the copolymer, a shampoo having the composition shown in Table 1-2 was prepared and evaluated in the same manner as in Example 1-1. Here, the viscosity of an aqueous solution containing 20 wt % of JR400 was higher than 100,000 mPa·s.

Comparative Examples 1-2 and 1-3

Preparation of Copolymers

Copolymers (1-8) and (1-9) were prepared in the same manner as for the preparation of copolymer (1-1) except that monomer compositions shown in Table 1-1 (copolymers (1-8) and (1-9)) were used. Of the obtained copolymers, the mol percents of the constituting units corresponding to the respective monomers in the entire constituting units, the weight average molecular weights and the viscosities of the 20% aqueous solution are shown in Table 1-1.

Preparation and Evaluation of Detergent Compositions

Using the obtained copolymers, shampoos having the compositions as shown in Table 1-2, were prepared and evaluated in the same manner as in Example 1-1. Here, each evaluation was carried out by using, as a comparative standard product, a composition which has the same composition as in Example 1-1, and which contains no copolymer (1-1). The results are shown in Table 1-3.

TABLE 1-3

| | | Example | | | | | | | | | | Comparative Example | | |
|---|---|---|---|---|---|---|---|---|---|---|---|---|---|---|
| | | 1-1 | 1-2 | 1-3 | 1-4 | 1-5 | 1-6 | 1-7 | 1-8 | 1-9 | 1-10 | 1-1 | 1-2 | 1-3 |
| Blending property | | 0 | 0 | 0 | 0 | 0 | −1 | 0 | −1 | 0 | −1 | 0 | 0 | −2 |
| Non-treated hair | Smoothness in rinsing | 0 | 1 | 1 | 2 | 2 | 1 | 2 | 2 | 2 | 2 | 1 | 0 | — |
| | Silky texture after drying | 1 | 2 | 1 | 2 | 2 | 2 | 2 | 2 | 2 | 2 | −1 | 0 | — |
| | Non-stiffness after drying | 1 | 2 | 1 | 1 | 1 | 1 | 2 | 2 | 2 | 2 | −1 | 0 | — |
| Damaged hair | Smoothness in rinsing | 0 | 1 | 1 | 2 | 2 | 1 | 2 | 2 | 2 | 2 | 1 | 0 | — |
| | Silky texture after drying | 1 | 2 | 1 | 2 | 1 | 2 | 2 | 2 | 2 | 2 | −1 | 0 | — |
| | Non-stiffness after drying | 1 | 2 | 1 | 1 | 1 | 1 | 1 | 2 | 2 | 2 | −1 | 0 | — |
| Total | | 4 | 10 | 6 | 10 | 9 | 7 | 11 | 11 | 12 | 11 | −2 | 0 | −2 |

As is evident from the foregoing results, the detergent compositions having the copolymers of the present invention incorporated have good blending properties, and with respect to both the non-treated hair and the damaged hair, they are excellent in the smoothness in rinsing, the silky texture after drying and non-stiffness after drying.

Further, as a conditioning polymer, the most important characteristic is the smoothness in rinsing. Accordingly, among those having the same overall points, one having a higher point for the smoothness in rinsing may be regarded as superior. From such a viewpoint, from the comparison between Examples 1-2 and 1-4 and between Example 1-6 and 1-7, it may be said that in the present invention, a detergent composition having incorporated a copolymer containing as a constituting component a cationic vinyl monomer having an amide bond, is superior.

On the other hand, in Comparative Example 1-1 employing JR400, the silky texture after drying was inferior, and stiffness was felt. Further, in Comparative Example 1-2 employing copolymer (1-8) having a low content of constituting units corresponding to the cationic vinyl monomer (A), the results obtained were not more than equal to the comparative standard product having no copolymer incorporated. Further, in Comparative Example 1-3 employing copolymer (1-9) having a high content of constituting units corresponding to the cationic vinyl monomer (A), it was not possible to obtain a uniform detergent composition.

Combined Use of Cationic Vinyl Monomers (A1) and (A2)

Example 2-1

Preparation of Copolymer

Into a reactor equipped with a reflux condenser, a dropping funnel, a thermometer, a nitrogen gas supply tube and a stirrer, 200 parts by weight of distilled water was charged, and in the dropping funnel, a monomer mixed liquid comprising 24 parts by weight of DMC (30 parts by weight as a 80 wt % aqueous solution), 23 parts by weight of DMAPAAC (31 parts by weight as a 75 wt % aqueous solution), 53 parts by weight of DMAA and 80 parts by weight of distilled water, was charged. The reactor was flushed with nitrogen and then heated to 90° C. To the reactor, 0.5 part by weight of 2,2'-azobis(2-methyl-N-(2-hydroxyethyl)-propionamide was put, and then the monomer mixed liquid was dropwise added over a period of 4 hours. After completion of the dropwise addition, a reaction was carried out for 20 hours, followed by cooling to obtain copolymer (2-1).

Of the obtained copolymer, the proportions of constituting units corresponding to the respective monomers in the entire constituting units, were DMC/DMAPAAC/DMAA=15/15/70 (mol percent). The weight average molecular weight was 380,000, and the viscosity of the 20 wt % aqueous solution was 580 mPa·s. The results are shown in Table 2-1.

Preparation of Detergent Composition

Using copolymer (2-1) obtained by the above method, a shampoo having the composition shown in Table 2-2 was prepared. The numerical values in the Table are all mass of active components.

Evaluation of Detergent Composition

Using the shampoo prepared by the above method, the blending property was evaluated by the above-mentioned method. Further, with respect to non-treated hair and damaged hair, the smoothness in rinsing, the finger-combing after towel-dry, the silky texture after drying and no stiffness after drying were evaluated. The results are shown in Table 2-3.

Examples 2-2 to 2-4

Preparation of Copolymers

Copolymers (2-2) to (2-4) were prepared in the same manner as in the preparation of copolymer (2-1) except that the monomer compositions shown in Table 2-1 (copolymers (2-2) to (2-4)) were used. Of the obtained copolymers, the mol percents of constituting units corresponding to the respective monomers in the entire constituting units, the weight average molecular weights and the viscosities of the 20% aqueous solutions were shown in Table 2-1.

Preparation and Evaluation of Detergent Compositions

Using the obtained copolymers, preparation and evaluation of shampoos having the compositions shown in Table 2-2 were carried out in the same manner as in Example 2-1. In Example 2-3, copolymer (2-3) had a relatively large content of the cationic groups whereby it was considered possible to obtain good performance even with a small amount, and accordingly, evaluation was carried out with a formulation wherein the blend amount was reduced as compared with other Examples. The results are shown in Table 2-3.

Examples 2-5 and 2-6

Using copolymer (2-1), shampoos having the compositions shown in Table 2-2 were prepared in the same manner as in Example 2-1. However, in the case where silicone oil was incorporated, the preparation was carried out firstly by mixing other than the silicone oil and then blending the silicone oil to the mixture. Then, evaluation of the shampoos was carried out. The results are shown in Table 2-3.

Comparative Examples 2-1 and 2-2

Preparation of Copolymers

Copolymers (2-5) and (2-6) were prepared in the same manner as in the preparation of copolymer (2-1) except that the monomer compositions shown in Table 2-1 (copolymers (2-5) and (2-6)) were used. Of the obtained copolymers, the mol percents of constituting units corresponding to the respective monomers in the entire constituting units, the weight average molecular weights and the viscosities of the 20% aqueous solutions were shown in Table 2-1.

Preparation and Evaluation of Detergent Compositions

Using the obtained copolymers, preparation and evaluation of shampoos having the compositions shown in Table 2-2 were carried out in the same manner as in Example 2-1. Here, each evaluation was carried out by using, as a comparative standard product, a composition having the same composition as in Example 2-1 and containing, instead of the copolymer (2-1), the same amount of JR400. The results are shown in Table 2-3.

TABLE 2-1

|  | Monomer composition (mass parts/mol percent) | | | | | Weight average | Viscosity of 20% aqueous |
|---|---|---|---|---|---|---|---|
|  | (A1) | (A2) | (B) | | | | |
|  | DMC | DMAPAAC | DMAA | DEAA | HEA | molecular weight *2 | solution (mPa · s) |
| Copolymer (2-1) | 24/15 | 23/15 | 53/70 | | | 380 k | 580 |
| Copolymer (2-2) | 14/10 | 21/15 | | 65/75 | | 370 k | 540 |
| Copolymer (2-3) | 59/42 | 4/3 | 37/55 | | | 310 k | 420 |
| Copolymer (2-4) | 14/10 | 29/20 | | | 57/70 | 240 k | 180 |
| Copolymer (2-5) | 58/40 | | 42/60 | | | 300 k | 400 |
| Copolymer (2-6) | | 37/25 | | | 63/75 | 240 k | 250 |

*1: Numerical values in Table all represent mass as solid contents.
*2: k represents 1,000.

TABLE 2-2

|  | Example | | | | | | Comparative Example | |
|---|---|---|---|---|---|---|---|---|
| Formulation | 2-1 | 2-2 | 2-3 | 2-4 | 2-5 | 2-6 | 2-1 | 2-2 |
| Copolymer (2-1) | 0.5 | | | | 0.5 | 0.5 | | |
| Copolymer (2-2) | | 0.5 | | | | | | |
| Copolymer (2-3) | | | 0.2 | | | | | |
| Copolymer (2-4) | | | | 0.5 | | | | |
| Copolymer (2-5) | | | | | | | 0.5 | |
| Copolymer (2-6) | | | | | | | | 0.5 |
| Anionic surfactant *2 | 10 | 10 | 10 | 10 | 10 | 10 | 10 | 10 |
| Amphoteric surfactant *3 | 4 | 4 | 4 | 4 | 4 | 4 | 4 | 4 |
| Semi-polar surfactant *4 | 1 | 1 | 1 | 1 | 1 | 1 | 1 | 1 |
| Cetanol | | | | | | 1 | | |
| Silicone oil *5 | | | | | 1 | | | |
| Distilled water | Rest | Rest | Rest | Rest | Rest | Rest | Rest | Rest |

*1: Numerical values in Table all represent mass as solid contents.
*2: Polyoxyethylene (3) lauryl ether sodium sulfate
*3: Lauramide propyl betaine
*4: Lauramine oxide
*5: Silicone emulsion BY22029 (50 mass % aqueous solution, manufactured by Dow Corning Toray)

TABLE 2-3

|  |  | Example | | | | | | Comparative Example | |
|---|---|---|---|---|---|---|---|---|---|
|  |  | 2-1 | 2-2 | 2-3 | 2-4 | 2-5 | 2-6 | 2-1 | 2-2 |
| Blending property | | 0 | 0 | −1 | 0 | −1 | 0 | 0 | 0 |
| Non-treated hair | Smoothness in rinsing | 2 | 1 | 1 | 1 | 2 | 2 | 0 | 0 |
|  | Finger-combing after towel-dry | 2 | 1 | 1 | 1 | 2 | 2 | 0 | 0 |
|  | Silky texture after drying | 2 | 1 | 2 | 1 | 2 | 2 | 2 | 1 |
|  | Non-stiffness after drying | 2 | 1 | 1 | 1 | 2 | 2 | 1 | 1 |
| Damaged hair | Smoothness in rinsing | 1 | 1 | 1 | 1 | 2 | 1 | 0 | 0 |
|  | Finger-combing after | 2 | 1 | 1 | 1 | 2 | 2 | 0 | 0 |

TABLE 2-3-continued

|  | Example | | | | | | Comparative Example | |
|---|---|---|---|---|---|---|---|---|
|  | 2-1 | 2-2 | 2-3 | 2-4 | 2-5 | 2-6 | 2-1 | 2-2 |
| towel-dry Silky texture after drying | 2 | 1 | 2 | 1 | 2 | 2 | 2 | 1 |
| Non-stiffness after drying | 1 | 1 | 1 | 0 | 2 | 1 | 0 | 0 |
| Total | 14 | 8 | 9 | 7 | 15 | 14 | 5 | 3 |

It is evident that the detergent compositions having the copolymers of the present invention incorporated, have good blending properties and with respect to both non-treated hair and damaged hair, exhibit smoothness in rinsing, good finger-combing, dry texture, etc., and even when compared with a composition containing a copolymer which contains only one type of a cationic vinyl monomer, they exhibit excellent performance, particularly in finger-combing after towel-dry.

Combined Use of Plural Copolymers Different in the Proportion of Cationic Monomer Preparation Example 3-1

Preparation of Copolymer

Into a reactor equipped with a reflux condenser, a is dropping funnel, a thermometer, a nitrogen gas supply tube and a stirrer, 200 parts by weight of distilled water was charged, and to the dropping funnel, a monomer mixture liquid comprising 34 parts by weight of DMC (43 parts by weight as a 80 wt % aqueous solution), 66 parts by weight of DMAA and 80 parts by weight of distilled water, was charged. The reactor was flushed with nitrogen and then heated to 90° C. To the reactor, 0.5 part by weight of 2,2'-azobis(2-methyl-N-(2-hydroxyethyl)-propionamide) was put, and then, the monomer mixture liquid was dropwise added over a period of 4 hours. After completion of the dropwise addition, the reaction was carried out for 20 hours, followed by cooling to obtain copolymer (3-1).

Of the obtained copolymer, the proportions of constituting units corresponding to the respective monomers in the entire constituting units were DMC/DMAA=20/80 (mol percent). The weight average molecular weight was 350,000, and the viscosity of the 20 wt % aqueous solution was 1,130 mPa·s. The results are shown in Table 3-1.

Preparation examples 3-2 to 3-5

Copolymers (3-2) to (3-5) were prepared in the same manner as in the preparation of copolymer (3-1) except that monomer compositions shown in Table 3-1 (copolymers (3-2) to (3-5)) were used. Of the obtained copolymers, the mol percents of constituting units corresponding to the respective monomers in the entire constituting units, the weight average molecular weights and the viscosities of the 20% aqueous solutions are shown in Table 3-1.

Preparation Example 3-6

Into reactor equipped with a reflux condenser, a dropping funnel, a nitrogen gas supply tube and a stirrer, 200 parts by weight of distilled water was charged, and to the dropping funnel, a monomer mixture unit comprising 58 parts by weight of DMC (73 parts by weight as a 80 wt % aqueous solution), 42 parts by weight of DMAA and 170 parts by weight of distilled water, was charged. The reactor was flushed with nitrogen and then heated to 80° C. To the reactor, 0.3 part by weight of 2,2'-azobis(2-methyl-N-(2-hydroxyethyl)-propionamide) was put, and then, the monomer mixed liquid was dropwise added over a period of 4 hours. After completion of the dropwise addition, the reaction was carried out for 20 hours, followed by cooling to obtain copolymer (3-6).

Of the obtained copolymer, the mol percents of constituting units corresponding to the respective monomers in the entire constituting units, the weight average molecular weight and the viscosity of the 20% aqueous solution, were shown in Table 3-1.

TABLE 3-1

| | Monomer composition (mass parts/mol percent) | | | | Weight average molecular weight *2 | Viscosity of 20% aqueous solution (mPa·s) |
|---|---|---|---|---|---|---|
| | (A) | | (B) | | | |
| | DMC | DMA-PAAC | DMAA | HEA | | |
| Copolymer (3-1) | 34/20 | | 66/80 | | 350 k | 1,130 |
| Copolymer (3-2) | 47/30 | | 53/70 | | 330 k | 850 |
| Copolymer (3-3) | 63/45 | | 37/55 | | 290 k | 520 |
| Copolymer (3-4) | 68/50 | | 32/50 | | 280 k | 300 |
| Copolymer (3-5) | | 49/35 | | 51/65 | 240 k | 250 |
| Copolymer (3-6) | 58/40 | | 42/60 | | 750 k | 58,200 |

*1: Numerical values in Table all represent mass as solid contents.
*2: k represents 1,000.

Example 3-1

Preparation Of Detergent Compositions

Using copolymers (3-2) and (3-3) obtained by the above method, shampoos having the compositions shown in Table 3-2 were prepared. The numerical values in the Table are all mass of the active components.

Evaluation of Detergent Compositions

Using the shampoos prepared by the above method, the blending properties were evaluated by the above-mentioned method. Further, with respect to non-treated hair and damaged hair, the smoothness in rinsing, the silky texture after drying and non-stiffness after drying, were evaluated. The results are shown in Table 3-3.

Examples 3-2 to 3-5

Preparation and Evaluation of Detergent Compositions

Preparation and evaluation of shampoos having the compositions shown in Table 3-2 were carried out in the same manner as in Example 3-1 except that those shown in Table 3-2 were used as the copolymers. However, in a case where silicone oil was incorporated, the preparation was carried out firstly by mixing other than the silicone oil, and then blending the silicone oil to the mixture. The results are shown in Table 3-3.

Comparative Examples 3-1 to 3-3

Preparation and Evaluation of Detergent Compositions

Preparation and evaluation of shampoos having the compositions shown in Table 3-2, were carried out in the same manner as in Example 3-1 except that those shown in Table 3-2 were used as the copolymers. The results are shown in Table 3-3.

Comparative Examples 3-4

Preparation and evaluation of a shampoo having the composition shown in Table 3-2 were carried out in the same manner as in Example 3-1, by using copolymer (3-2) and JR400. Here, each evaluation was carried out by using, as a comparative standard product, one having the composition of Example 3-1 wherein only copolymer (3-2) was used in an amount of 0.4 parts by weight.

TABLE 3-2

|  | Example | | | | | Comparative Example | | | |
|---|---|---|---|---|---|---|---|---|---|
|  | 3-1 | 3-2 | 3-3 | 3-4 | 3-5 | 3-1 | 3-2 | 3-3 | 3-4 |
| Copolymer (3-1) |  |  |  |  |  | 0.4 |  |  |  |
| Copolymer (3-2) | 0.3 | 0.4 | 0.4 | 0.4 | 0.4 |  | 1.0 |  | 0.3 |
| Copolymer (3-3) | 0.2 |  |  |  |  |  |  |  |  |
| Copolymer (3-4) |  |  |  |  |  | 0.1 |  |  |  |
| Copolymer (3-5) |  | 0.2 |  |  |  |  |  | 0.4 |  |
| Copolymer (3-6) |  |  | 0.2 | 0.2 | 0.2 |  |  |  |  |
| JR400 |  |  |  |  |  |  |  |  | 0.2 |
| Anionic surfactant *2 | 10 | 10 | 10 | 10 | 10 | 10 | 10 | 10 | 10 |
| Ampho-teric surfactant *3 | 4 | 4 | 4 | 4 | 4 | 4 | 4 | 4 | 4 |
| Nonionic surfactant *4 | 0.7 | 0.7 | 0.7 | 0.7 | 0.7 | 0.7 | 0.7 | 0.7 | 0.7 |
| Semi-polar surfactant *5 | 0.7 | 0.7 | 0.7 | 0.7 | 0.7 | 0.7 | 0.7 | 0.7 | 0.7 |
| Cetanol |  |  |  |  |  |  | 1 | 1 |  |
| Silicone oil *6 |  |  |  |  |  |  |  | 1 |  |
| Distilled water | Rest | Rest | Rest | Rest | Rest | Rest | Rest | Rest | Rest |

*1: Numerical values in Table all represent mass as solid contents.
*2: Polyoxyethylene (3) lauryl ether sodium sulfate
*3: Lauramide propyl betaine
*4: Lauric acid diethanol amide
*5: Lauramine oxide
*6: Silicone emulsion BY22029 (50 mass % aqueous solution, manufactured by Dow Corning Toray)

TABLE 3-3

|  |  | Example | | | | | Comparative Example | | | |
|---|---|---|---|---|---|---|---|---|---|---|
|  |  | 3-1 | 3-2 | 3-3 | 3-4 | 3-5 | 3-1 | 3-2 | 3-3 | 3-4 |
| Blending property |  | −1 | 0 | 0 | −1 | −1 | −1 | 0 | 0 | 0 |
| Non-treated hair | Smoothness in rinsing | 1 | 2 | 1 | 2 | 2 | 1 | 0 | 1 | 1 |
|  | Silky texture after drying | 2 | 2 | 2 | 2 | 2 | 1 | 0 | −1 | 0 |
|  | Non-stiffness after drying | 1 | 1 | 2 | 2 | 2 | 0 | 0 | 0 | −1 |
| Damaged hair | Smoothness in rinsing | 1 | 2 | 1 | 1 | 2 | 1 | 0 | 0 | 1 |
|  | Silky texture after drying | 2 | 1 | 2 | 2 | 2 | 1 | 0 | −1 | 0 |
|  | Non-stiffness after drying | 1 | 1 | 2 | 2 | 2 | 0 | 0 | 0 | −1 |
| Total |  | 7 | 9 | 10 | 10 | 11 | 3 | 0 | −1 | 0 |

The detergent compositions of the present invention are excellent as having excellent smoothness, silky texture, etc. with respect to both non-treated hair and damaged hair, as compared with Comparative Example 3-2 and 3-3 wherein only one type of copolymer is incorporated. Further, they have excellent performance as compared also with Comparative Example 3-4 wherein one type of copolymer is used in combination with a cationic cellulose or Comparative Example 3-1 wherein two types of copolymers wherein the contents of the cationic vinyl monomers are outside the scope of the present invention, are used in combination.

Combined Use of Plural Copolymers Different in the Type Of Cationic Monomer

Example 4-1

Preparation of Copolymer

Into a reactor equipped with a reflux condenser, a dropping funnel, a thermometer, a nitrogen gas supply tube and a stirrer, 200 parts by weight of distilled water was charged, and to the dropping funnel, a monomer mixed liquid comprising 47 parts by weight of DMC (59 parts by weight as a 80 wt % aqueous solution), 53 parts by weight of DMAA and 80 parts by weight of distilled water, was charged. The reactor was flushed with nitrogen and then heated to 90° C. To the reactor, 0.5 part by weight of 2,2'-azobis(2-methyl-N-(2-hydroxyethyl)propionamide) was put, and then, the monomer mixed liquid was dropwise added over a period of 4 hours. After completion of the dropwise addition, the reaction was carried out for 20 hours, followed by cooling to obtain copolymer (4-1).

Of the obtained copolymer, the proportions of constituting units corresponding to the respective monomers in the entire constituting units were DMC/DMAA=30/70 (mol percent). The weight average molecular weight was 330,000, and the viscosity of the 20 wt % aqueous solution was 850 mPa·s. The results are shown in Table 4-1.

Preparation examples 4-2 to 4-5

Copolymers (4-2) to (4-5) were prepared in the same manner as in the preparation of copolymer (4-1) except that the monomer compositions shown in Table 4-1 (copolymers (4-2) to (4-5)) were used. Of the obtained copolymers, the mol percents of constituting units corresponding to the respective monomers in the entire constituting units, the weight average molecular weights and the viscosities of the 20% aqueous solutions were shown in Table 4-1.

TABLE 4-1

|  | Monomer composition (mass parts/mol percent) | | | | | | Weight average molecular weight *2 | Viscosity of 20% aqueous solution (mPa · s) |
|---|---|---|---|---|---|---|---|---|
|  | (A1) | (A2) | (B) | | | | | |
|  | DMC | DMAPAAC | DMAA | DEAA | HEMA | HEA | | |
| Copolymer (4-1) | 47/30 |  | 53/70 |  |  |  | 330 k | 850 |
| Copolymer (4-2) | 52/40 |  |  | 48/60 |  |  | 300 k | 350 |
| Copolymer (4-3) | 37/25 |  |  |  |  | 63/75 | 230 k | 100 |
| Copolymer (4-4) |  | 47/30 | 53/70 |  |  |  | 430 k | 1,490 |
| Copolymer (4-5) |  | 41/30 |  |  | 59/70 |  | 230 k | 440 |

*1: Numerical values in Table all represent mass as solid contents.
*2: k represents 1,000.

Example 4-1

Preparation of Detergent Compositions

Using copolymers (4-1) and (4-4) obtained by the above method, shampoos having the compositions shown in Table 4-2 were prepared. The numerical values in the Table are all mass of the active components.
Evaluation of Detergent Compositions
Using the shampoos prepared by the above method, the blending properties were evaluated by the above-mentioned method. Further, with respect to non-treated hair and damaged hair, the smoothness in rinsing, the silky texture after drying and non-stiffness after drying were evaluated. The results are shown in Table 4-3.

Examples 4-2 to 4-7

Preparation and Evaluation of Detergent Compositions

Preparation and evaluation of shampoos having the compositions shown in Table 4-2 were carried out in the same manner as in Example 4-1 except that those shown in Table 4-2 were used as the copolymers. However, in a case where silicone oil was incorporated, the preparation was carried out firstly by mixing other than the silicone oil, and then blending the silicone oil to the mixture.
The results are shown in Table 4-3.

Comparative Examples 4-1

Preparation and Evaluation of Detergent Compositions

Preparation and evaluation of a shampoo having the composition shown in Table 4-2, were carried out in the same manner as in Example 4-1 except that one shown in Table 4-2 was used as the copolymers. The results are shown in Table 4-3.

Comparative Examples 4-2

Preparation and evaluation of a shampoo having the composition shown in Table 4-2 were carried out in the same manner as in Example 4-1, by using copolymer (4-1) and JR400. Here, each evaluation was carried out by using, as a comparative standard product, one having a composition of Example 4-1 wherein only copolymer (4-1) was used in an amount of 0.4 parts by weight. The results are shown in Table 4-3.

TABLE 4-2

|  | Example | | | | | | | Comparative Example | |
|---|---|---|---|---|---|---|---|---|---|
|  | 4-1 | 4-2 | 4-3 | 4-4 | 4-5 | 4-6 | 4-7 | 4-1 | 4-2 |
| Copolymer (4-1) | 0.4 |  |  | 0.3 |  | 0.4 | 0.4 |  | 0.4 |
| Copolymer (4-2) |  | 0.4 |  |  |  |  |  |  |  |
| Copolymer (4-3) |  |  | 0.5 |  | 0.4 |  |  |  |  |
| Copolymer (4-4) | 0.2 | 0.2 | 0.2 |  |  | 0.2 | 0.2 | 0.3 |  |
| Copolymer (4-5) |  |  |  | 0.3 | 0.4 |  |  |  |  |
| JR400 |  |  |  |  |  |  |  |  | 0.2 |
| Anionic surfactant *2 | 10 | 10 | 10 | 10 | 10 | 10 | 10 | 10 | 10 |
| Amphoteric surfactant *3 | 4 | 4 | 4 | 4 | 4 | 4 | 4 | 4 | 4 |
| Semipolar surfactant *4 | 1 | 1 | 1 | 1 | 1 | 1 | 1 | 1 | 1 |
| Cetanol |  |  |  |  |  | 1 | 1 |  |  |
| Silicone oil *5 |  |  |  |  |  |  | 1 |  |  |
| Distilled water | Rest | Rest | Rest | Rest | Rest | Rest | Rest | Rest | Rest |

*1: Numerical values in Table all represent mass as solid contents.
*2: Polyoxyethylene (3) lauryl ether sodium sulfate
*3: Lauramide propyl betaine
*4: Lauramine oxide
*5: Silicone emulsion BY22029 (50 mass % aqueous solution, manufactured by Dow Corning Toray)

TABLE 4-3

|  |  | Example | | | | | | | Comparative Example | |
|---|---|---|---|---|---|---|---|---|---|---|
|  |  | 4-1 | 4-2 | 4-3 | 4-4 | 4-5 | 4-6 | 4-7 | 4-1 | 4-2 |
| Blending property |  | 0 | −1 | 0 | 0 | 0 | −1 | −1 | 0 | 0 |
| Non-treated hair | Smoothness in rinsing | 2 | 2 | 1 | 1 | 1 | 2 | 2 | 1 | 1 |
|  | Silky texture after drying | 2 | 1 | 1 | 2 | 0 | 2 | 2 | −1 | −1 |
|  | Non-stiffness after drying | 1 | 1 | 0 | 1 | 1 | 2 | 2 | 0 | −1 |

TABLE 4-3-continued

|  |  | Example | | | | | | | Comparative Example | |
|---|---|---|---|---|---|---|---|---|---|---|
|  |  | 4-1 | 4-2 | 4-3 | 4-4 | 4-5 | 4-6 | 4-7 | 4-1 | 4-2 |
| Damaged hair | Smoothness in rinsing | 2 | 2 | 1 | 1 | 1 | 2 | 2 | 1 | 1 |
|  | Silky texture after drying | 1 | 1 | 1 | 1 | 0 | 2 | 2 | −1 | −1 |
|  | Non-stiffness after drying | 1 | 1 | 0 | 1 | 1 | 1 | 2 | 0 | −1 |
| Total |  | 9 | 7 | 4 | 7 | 4 | 10 | 11 | 0 | −2 |

The detergent compositions of the present invention are excellent as having excellent smoothness, silky texture, etc. with respect to both non-treated hair and damaged hair, as compared with Comparative Example 4-1, wherein only one type of copolymer is incorporated. Further, they have excellent performance as compared also with Comparative Example 4-2, wherein one of copolymer is used in combination with a cationic cellulose.

INDUSTRIAL APPLICABILITY

The copolymer of the present invention exhibits, when incorporated into a detergent composition, excellent conditioning effects. Namely, it is capable of improving the smoothness of the surface of an object to be washed during washing, such as the skin or hair and also protecting the surface of the object after drying. Accordingly, it is effectively useful as a shampoo or a body soap excellent in foaming, smoothness in rinsing, finger-combing after towel-dry, and silky texture, non-stiffness and flexibility after drying.

The entire disclosures of Japanese Patent Application No. 2005-227247 filed on Aug. 4, 2005, Japanese Patent Application No. 2005-227248 filed on Aug. 4, 2005, Japanese Patent Application No. 2005-227249 filed on Aug. 4, 2005 and Japanese Patent Application No. 2005-227250 filed on Aug. 4, 2005 including specifications, claims and summaries are incorporated herein by reference in their entireties.

The invention claimed is:

1. A detergent composition, comprising:
at least one copolymer; and
at least one surfactant;
wherein,
the at least one copolymer comprises as constituting units:
a cationic vinyl monomer (A); and
a vinyl monomer (B);
wherein
the cationic vinyl monomer (A), comprises:
a monomer (A2) of formula (3) wherein c is 0, and
optionally a monomer (A1) of formula (3) wherein c is 1,

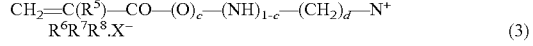

$$CH_2=C(R^5)-CO-(O)_c-(NH)_{1-c}-(CH_2)_d-N^+R^6R^7R^8.X^- \quad (3)$$

wherein $R^5$ is a hydrogen atom or a methyl group, each of $R^6$ and $R^7$ which are independent of each other, is a $C_{1-24}$ alkyl group, an aryl group or an aralkyl group, $R^8$ is a hydrogen atom, a $C_{1-24}$ alkyl group, an aryl group, an aralkyl group or $-CH_2-CH(OH)-CH_2-N^+R^9R^{10}R^{11}.Y-$, each of $R^9$ to $R^{11}$ which are independent of one another, is a $C_{1-24}$ alkyl group, an aryl group or an aralkyl group, each of $X^-$ and $Y^-$ which are independent of each other, is an anion, c is 0 or 1, and d is an integer of from 1 to 10,
the vinyl monomer (B), comprises:
a monomer of formula (I)

$$CH_2=C(R^1)-CO-NR^2R^3 \quad (1)$$

wherein $R^1$ is a hydrogen atom or a methyl group, and each of $R^2$ and $R^3$ which are independent of each other, is a hydrogen atom or a $C_{1-3}$ alkyl group, provided that the sum of carbon numbers of $R^2$ and $R^3$ is from 1 to 4, or 2,3-dihydroxypropyl(meth)acrylate, and
wherein
a proportion of the cationic vinyl monomer (A) is from 25 to 45 mol % based on the entire copolymer, and
the copolymer comprises no cross-linking agent as a component.

2. The detergent composition according to claim 1, which comprises at least a copolymer (C1) and a copolymer (C2), wherein the proportion of cationic vinyl monomer (A) in the copolymer (C2) is larger than the proportion of cationic vinyl monomer (A) in the copolymer (C1).

3. The detergent composition according to claim 1, which comprises at least a copolymer (C3) and a copolymer (C4), wherein
the copolymer (C3) comprises: a vinyl monomer of the formula (I) or 2,3-dihydroxypropyl(meth)acrylate, and a monomer (A1), and
the copolymer (C4) comprises a vinyl monomer of the formula (I) or 2,3-dihydroxypropyl(meth)acrylate, and a monomer (A2).

4. The detergent composition according to claim 1, wherein the surfactant, comprises at least an anionic surfactant.

5. The detergent composition according to claim 4, wherein
a content of the anionic surfactant is from 5 to 40 wt %,
a content of the copolymer is from 0.01 to 5 wt %, and
the detergent further comprises from 0 to 10 wt %, of at least one surfactant selected from the group consisting of an amphoteric surfactant, a nonionic surfactant and a semi-polar surfactant.

6. The detergent composition according to claim 1, which further comprises a silicone oil, a higher alcohol or a mixture thereof.

7. The detergent composition according to claim 1, wherein a proportion of the vinyl monomer (B) is from 20 to 75 mol % based on the entire copolymer.

8. The detergent composition according to claim 1, wherein
a proportion of the monomer (A1) is from 1 to 44 mol %,
a proportion of the monomer (A2) is from 1 to 44 mol %, and
the total of the proportions of monomer (A1) and monomer (A2) is from 25 to 45 mol %, based on the entire copolymer.

9. The detergent composition according to claim 1, wherein a weight average molecular weight of the obtained copolymer is from 10,000 to 2,000,000.

10. The detergent composition according to claim 1, wherein the copolymer comprises at least the vinyl monomer (B) of the formula (1).

* * * * *